(12) United States Patent
Sano et al.

(10) Patent No.: US 12,105,033 B2
(45) Date of Patent: Oct. 1, 2024

(54) INSPECTION SYSTEM, DETERMINATION PROCESSING APPARATUS, AND INSPECTION METHOD

(71) Applicant: JGC CORPORATION, Kanagawa (JP)

(72) Inventors: Teruaki Sano, Kanagawa (JP); Kiminori Shigetomi, Kanagawa (JP); Shigeo Otsuki, Kanagawa (JP); Nobutaka Tanaka, Kanagawa (JP)

(73) Assignee: JGC CORPORATION, Kanagawa (JP)

( * ) Notice: Subject to any disclaimer, the term of this patent is extended or adjusted under 35 U.S.C. 154(b) by 371 days.

(21) Appl. No.: 17/638,176

(22) PCT Filed: Jul. 16, 2020

(86) PCT No.: PCT/JP2020/027719
§ 371 (c)(1),
(2) Date: Feb. 24, 2022

(87) PCT Pub. No.: WO2022/014019
PCT Pub. Date: Jan. 20, 2022

(65) Prior Publication Data
US 2022/0299451 A1 Sep. 22, 2022

(51) Int. Cl.
*G01N 23/04* (2018.01)
*G01N 23/083* (2018.01)
(Continued)

(52) U.S. Cl.
CPC ........... *G01N 23/04* (2013.01); *G01N 23/083* (2013.01); *G01N 33/2045* (2019.01);
(Continued)

(58) Field of Classification Search
CPC .. G01N 23/04; G01N 33/207; G01N 33/2045; G01N 23/083; G01N 2223/04;
(Continued)

(56) References Cited

U.S. PATENT DOCUMENTS

RE47,918 E * 3/2020 Wallace ............... B23K 9/0953
2012/0201347 A1 8/2012 Prentice et al.

FOREIGN PATENT DOCUMENTS

JP H0260861 5/1990
JP H0896136 4/1996
(Continued)

OTHER PUBLICATIONS

Yang et al, "Deep Learning Based Steel Pipe Weld Defect Detection", 2021, Applied Artificial Intelligence, 35:15, 1237-1249, DOI: 10.1080/08839514.2021. 1975391 (14 pages) (Year: 2021).*
(Continued)

*Primary Examiner* — David F Dunphy
(74) *Attorney, Agent, or Firm* — JCIPRNET (57) ABSTRACT

In a nondestructive inspection of a defect of a welded portion of a pipe or a pipe member, work efficiency of a radiation transmission test is improved by reducing a burden on a worker, and an inspection accuracy is improved. Imaging data is acquired by transmitting radiation through a welded portion of the pipe to be inspected. Processing of associating determination data indicating a result of determining a defect of the welded portion of the pipe to be inspected based on a distribution of a transmission intensity of the radiation obtained from the imaging data with image data showing the distribution of the transmission intensity of the radiation is performed. As a result, through use of the imaging data, image data and determination data associated with the image data can be obtained, and the burden on the worker can be reduced.

11 Claims, 9 Drawing Sheets

(51) Int. Cl.
  *G01N 33/2045* (2019.01)
  *G01N 33/207* (2019.01)
  *G01T 7/00* (2006.01)
  *G06T 7/00* (2017.01)

(52) U.S. Cl.
  CPC ......... *G01N 33/207* (2019.01); *G06T 7/001* (2013.01); *G01N 2223/04* (2013.01); *G01N 2223/3303* (2013.01); *G01N 2223/401* (2013.01); *G01N 2223/628* (2013.01); *G01N 2223/629* (2013.01); *G01N 2223/646* (2013.01); *G06T 2207/10116* (2013.01); *G06T 2207/20081* (2013.01); *G06T 2207/20212* (2013.01); *G06T 2207/30136* (2013.01)

(58) Field of Classification Search
  CPC ..... G01N 2223/3303; G01N 2223/401; G01N 2223/628; G01N 2223/629; G01N 2223/646; G06T 7/001; G06T 2207/10116; G06T 2207/20081; G06T 2207/20212; G06T 2207/30136
  See application file for complete search history.

(56) References Cited

FOREIGN PATENT DOCUMENTS

| | | |
|---|---|---|
| JP | 2000180387 | 6/2000 |
| JP | 2009047424 | 3/2009 |
| JP | 2013195119 | 9/2013 |
| JP | 2018025497 | 2/2018 |
| JP | 2018179857 | 11/2018 |
| JP | 2019095247 | 6/2019 |
| WO | 2017130477 | 8/2017 |
| WO | 2019059011 | 3/2019 |

OTHER PUBLICATIONS

"Office Action of Japan Counterpart Application" with English translation thereof, issued on Feb. 15, 2022, p. 1-p. 7.
"Office Action of Japan Counterpart Application" with English translation thereof, issued on Aug. 9, 2022, p. 1-p. 8.
"International Search Report (Form PCT/ISA/210) of PCT/JP2020/027719," mailed on Sep. 29, 2020, with English translation thereof, pp. 1-5.

* cited by examiner

(a) image data (b) image data with which determination data is associated

INSPECTION SYSTEM, DETERMINATION PROCESSING APPARATUS, AND INSPECTION METHOD

CROSS-REFERENCE TO RELATED APPLICATION

This application is a 371 application of the international PCT application serial no. PCT/JP2020/027719, filed on Jul. 16, 2020. The entirety of each of the above-mentioned patent applications is hereby incorporated by reference herein and made a part of this specification.

TECHNICAL FIELD

The present disclosure relates to a technology for performing a nondestructive inspection of a welded portion of a pipe.

BACKGROUND ART

Examples of a plant for processing fluid include a natural gas plant for, for example, liquefying natural gas and separating/recovering a natural gas liquid, a petroleum refining plant for, for example, distilling and desulfurizing crude oil or various intermediate products, and a chemical plant for producing a petrochemical product, an intermediate chemical product, a polymer, and the like.

Those plants have a structure in which a large number of equipment groups including static equipment, such as tower and tanks, and heat exchangers, and dynamic equipment, such as pumps, are arranged. Further, pipes for transferring and receiving fluids are connected between pieces of equipment forming those equipment groups.

In construction of such a plant, welding may be used to connect pipes or connect a pipe and a pipe member, for example, a flange or an elbow. When there is a flaw (a harmful flaw that exceeds a permissible degree and is determined to be a failure is hereinafter referred to as a "defect") having a size or shape exceeding a permissible degree is present in the welded portion in which the welding has been performed, after the plant starts to operate, the flaw can become a factor in causing problems such as fluid leakage and fracturing of the welded portion. Therefore, after the pipe or pipe member has been welded, in order to determine whether or not a defect is present in the pipe welded portion, a radiation transmission test is performed in accordance with a sampling frequency set by taking into consideration a plurality of elements such as the fluid and pressure to which the pipe and pipe member are exposed.

Hitherto, when a radiation transmission test on a welded portion is performed, whether or not a flaw or defect is present in the welded portion is examined by irradiating the welded portion with radiation such as y-rays or X-rays, and exposing an industrial film mounted behind the welded portion with the radiation that has been transmitted through the welded portion. The presence or absence of a flaw and the determination of a defect are tasks performed by a qualified person visually evaluating the imaged film in a dark room.

The imaging of the welded portion using radiation is a task which requires a safe distance to be maintained, and therefore there is a limit to the number of times for which the imaging task can be performed simultaneously in a limited construction area. Further, it takes time to arrange each imaging site, and therefore the impact on the overall construction schedule of the plant is required to be taken into consideration. Moreover, the number of welded portions that are welded when a plant is constructed is very large, and therefore it is also required to work with a large quantity of films corresponding to the number of welded portions. Further, it is also required to manage and dispose of developer for developing the films, and therefore consideration for the environment is also required.

In order to solve such various problems, it is required to establish an inspection technology for welded portions which can improve work efficiency and further reduce burdens on workers.

In Patent Literature 1, there is described a radiation inspection apparatus for irradiating a pipe to be inspected in a plant with radiation from a radiation source, detecting the transmitted radiation with a detector, and inspecting a thickness of the pipe to be inspected. Further, there is described a configuration in which angles of the radiation source and the detector with respect to the pipe are rotated, and transmission images are acquired at different rotation angles. Further, in Patent Literature 2, there is described a maintenance support apparatus for measuring a decrease in the thickness of a structure of the plant, acquiring a standardization constant from the measured value, and calculating a probability of the structure becoming unusable for each combination of a predetermined use period and thickness based on the standardization constant.

In this way, hitherto, methods of detecting the transmission amount of radiation without using a film have only been used for the management of a decrease in the thickness of a pipe in an operating plant.

CITATION LIST

Patent Literature

[PTL 1] JP 2009-47424 A
[PTL 2] JP 2018-25497 A

SUMMARY OF INVENTION

Technical Problem

The present disclosure is to provide a technology for improving work efficiency of a radiation transmission test by reducing a burden on a worker and improving inspection accuracy in a nondestructive inspection of a defect of a welded portion of a pipe or a pipe member.

Solution to Problem

According to one embodiment of the present disclosure, there is provided an inspection system of a nondestructive inspection of a defect of a welded portion of a pipe or a pipe member, the inspection system including: an imaging data acquisition unit configured to acquire imaging data obtained by transmitting radiation through the welded portion of the pipe or pipe member to be inspected; and a determination processing unit configured to perform processing of associating, with image data showing a distribution of a transmission intensity of the radiation obtained from the imaging data, determination data indicating a result of determining a defect of the welded portion to be inspected based on the distribution of the transmission intensity of the radiation.

Further, the inspection system may have the following features.

(a) An imaging data acquisition unit includes: a radiation irradiation unit configured to irradiate radiation in a direction of the welded portion; and a detector configured to detect the radiation transmitted through the welded portion, the radiation irradiation unit and the detector are arranged so as to face each other across the welded portion to be inspected, and the imaging data is acquired as digital data based on the transmission intensity of the radiation detected by the detector.

(b) The imaging data acquisition unit includes: a jig for arranging the radiation irradiation unit and the detector so as to face each other across the welded portion to be inspected; and a movement mechanism configured to move, while maintaining a state in which the radiation irradiation unit and the detector are arranged so as to face each other by the jig, a position to irradiate the radiation in a circumferential direction of the welded portion by moving the radiation irradiation unit and the detector in the circumferential direction with the radiation irradiation unit and the detector remaining in synchronization, and the imaging data is individually acquired at a plurality of different positions in the circumferential direction of the welded portion.

(c) The inspection system further includes an image processing unit configured to create the image data by combining, along the circumferential direction of the welded portion, a plurality of pieces of the imaging data acquired at a plurality of positions different in the circumferential direction.

(d) An analog image obtained by irradiating an area including the welded portion to be inspected with radiation and exposing a radiation image transmitted through the welded portion onto a film is converted to a digital image, and the digital image is used as the imaging data.

(e) The determination data is associated with information with which a position of a flaw in a welding line included in the image data, a size of the flaw, and a shape feature of the flaw are identifiable, and includes information indicating a type of a defect which is a harmful flaw for which a result of the welding of the welded portion is determined to be a failure, the inspection system further includes an automatic determination unit configured to associate, based on results obtained by performing machine learning of flaws included in past image data with which the determination data is associated, preliminary determination data obtained by automatically determining a type of a predicted defect by identifying the position, size, and shape feature of the flaw in the welding line, with image data showing a new distribution of the transmission intensity of the radiation, and the determination processing unit is configured to perform the processing of associating the determination data with the image data by performing the determination based on the preliminary determination data associated with the image data by the automatic determination processing unit.

(f) The determination processing unit is configured to be able to receive processing of correcting the preliminary determination data associated with the image data by the automatic determination unit.

According to one embodiment of the present disclosure, there is provided a determination processing apparatus for performing determination processing of a nondestructive inspection of a defect of a welded portion of a pipe or a pipe member, the determination processing apparatus being configured to perform processing of associating determination data indicating a result of determining the defect of the welded portion of the pipe to be inspected based on a distribution of a transmission intensity of radiation obtained by transmitting the radiation through the welded portion of the pipe or pipe member to be inspected, with image data showing the distribution of the transmission intensity of the radiation.

According to one embodiment of the present disclosure, there is provided an inspection method for a nondestructive inspection of a defect of a welded portion of a pipe or a pipe member, the inspection method including a step of performing processing of associating determination data indicating a result of determining the defect of the welded portion to be inspected based on a distribution of a transmission intensity of radiation obtained by transmitting the radiation through the welded portion of the pipe or pipe member to be inspected, with image data showing the distribution of the transmission intensity of the radiation.

Advantageous Effects of Invention

In the present disclosure, in the nondestructive inspection of the defect of the welded portion of the pipe or the pipe member, imaging data obtained by transmitting radiation through the welded portion of the pipe or the pipe member to be inspected is acquired. Further, through use of the imaging data, the defect of the welded portion to be inspected is determined, and the processing of associating the determination data indicating the determination result with image data showing the distribution of the transmission intensity of the radiation is performed. Therefore, the determination result of the welded portion can be obtained without using a film, and the work efficiency of the radiation transmission test can be improved by reducing the burden on the worker. Further, through use of image data, the inspection accuracy and inspection efficiency can be improved compared to visual determination using the film.

DESCRIPTION OF EMBODIMENTS

Figure 1:
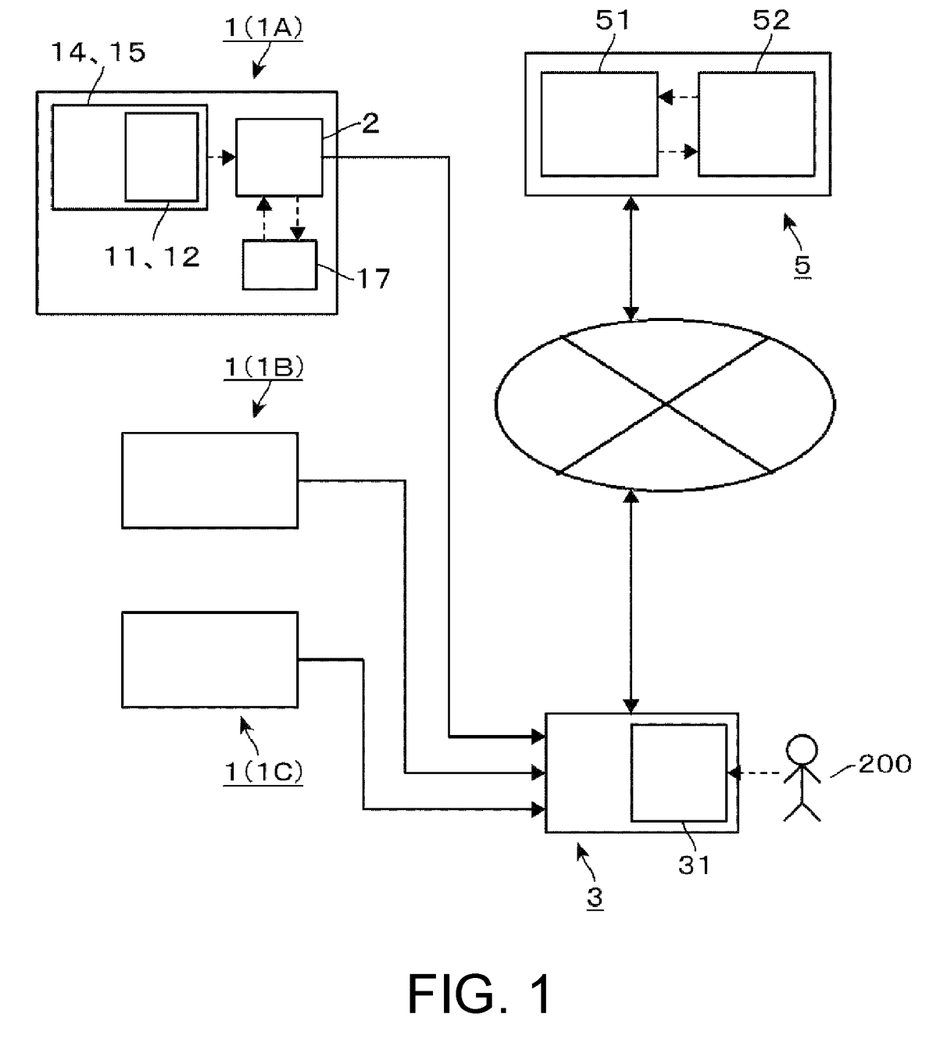
FIG. 1 is a configuration diagram of an inspection system for nondestructively inspecting a welded portion of a pipe.

FIG. 1 shows an overall configuration of an inspection system of a radiation transmission test of a defect of a welded portion of a pipe or a pipe member. In the radiation transmission test in an embodiment of the present disclosure, a radiation transmission test of a welded portion of a pipe or a pipe member is performed based on results obtained by performing imaging using radiation. Then, based on image data showing a distribution of a transmission intensity of the radiation obtained by imaging, the presence or absence of a flaw in the welded portion is checked, and when there is a flaw, it is determined whether or not the flaw corresponds to a "defect," which is a harmful flaw for which the result of the welding is determined to be a failure.

For example, this technology is applied to a nondestructive inspection of a welded portion in the construction and maintenance of a plant in which pipes which transport fluids via the pipes are arranged. There is no particular limitation on the type of plant to which this technology is applied, and this technology may be applied to a nondestructive inspection of welded portions in, for example, natural gas plants for, for example, liquefying natural gas and separating/recovering natural gas liquids, petroleum refining plants for, for example, distilling and desulfurizing crude oil or various intermediate products, chemical plants for, for example, producing petrochemical products, intermediate chemical products, polymers, and the like, pharmaceutical plants for producing pharmaceuticals and intermediate products, and waste disposal plants for low-level radioactive waste.

The pipe to which this technology is applied may be any pipe which is connected by welding and on which a radiation transmission test can be performed. There is no particular limitation on a material of the pipe, a pipe diameter, wall thickness, presence or absence of a lining, for example. Further, in addition to gases and liquids, the fluid flowing in the pipe may be a particulate matter (for example, a powder, particles, or pellets) having fluidity.

The pipe member to which this technology is applied is a non-pipe component used to connect equipment to be arranged in the plant by a pipe. Examples of the pipe member may include flanges, elbows, T-fittings, different-diameter pipe fittings, and the like. Regarding the pipe member as well, the pipe member is not particularly limited in terms of its material, size, wall thickness, presence or absence of a lining, and the like, as long as the pipe member is connected by welding and can be subjected to a radiation transmission test.

The welded portion subjected to the radiation transmission test may be any of a welded portion between pipes, a welded portion between a pipe and a pipe member, and a welded portion between pipe members.

Next, there is described a configuration example of the inspection system of this example. The inspection system includes imaging data acquisition units 1 (1A to 1C) for transmitting radiation, for example, y-rays or X-rays, onto the welded portion of the pipe or pipe member to be inspected, and acquiring imaging data as digital data. Further, the inspection system includes a determination processing unit 3 for creating, based on the image data showing the distribution of the transmission intensity of the radiation obtained from the imaging data, determination data indicating the result of a determination of a defect of the welded portion of the pipe or pipe member to be inspected, and performing processing of associating the determination data with the image data. For example, the determination processing unit 3 is built from a computer.

The flaw included in a welded portion 81 corresponds to a defect, and the determination of whether the welding result is a failure is performed by a qualified person authorized by a public organization or a private organization, for example.

In regard to this, the inspection system of this example includes an automatic determination unit 5 for providing preliminary determination data which supports the determination when the qualified person performs the determination. The automatic determination unit 5 includes a storage unit 51 for storing the image data and the determination data, and an arithmetic unit 52 for performing machine learning of image information on the flaw and automatically determining the type of the defect included in the image data based on the results of the machine learning. For example, as illustrated in FIG. 1, the automatic determination unit 5 can be provided as a cloud computing function, and is configured such that the automatic determination unit 5 can be accessed via the Internet or the like from the determination processing unit 3.

Figure 2:
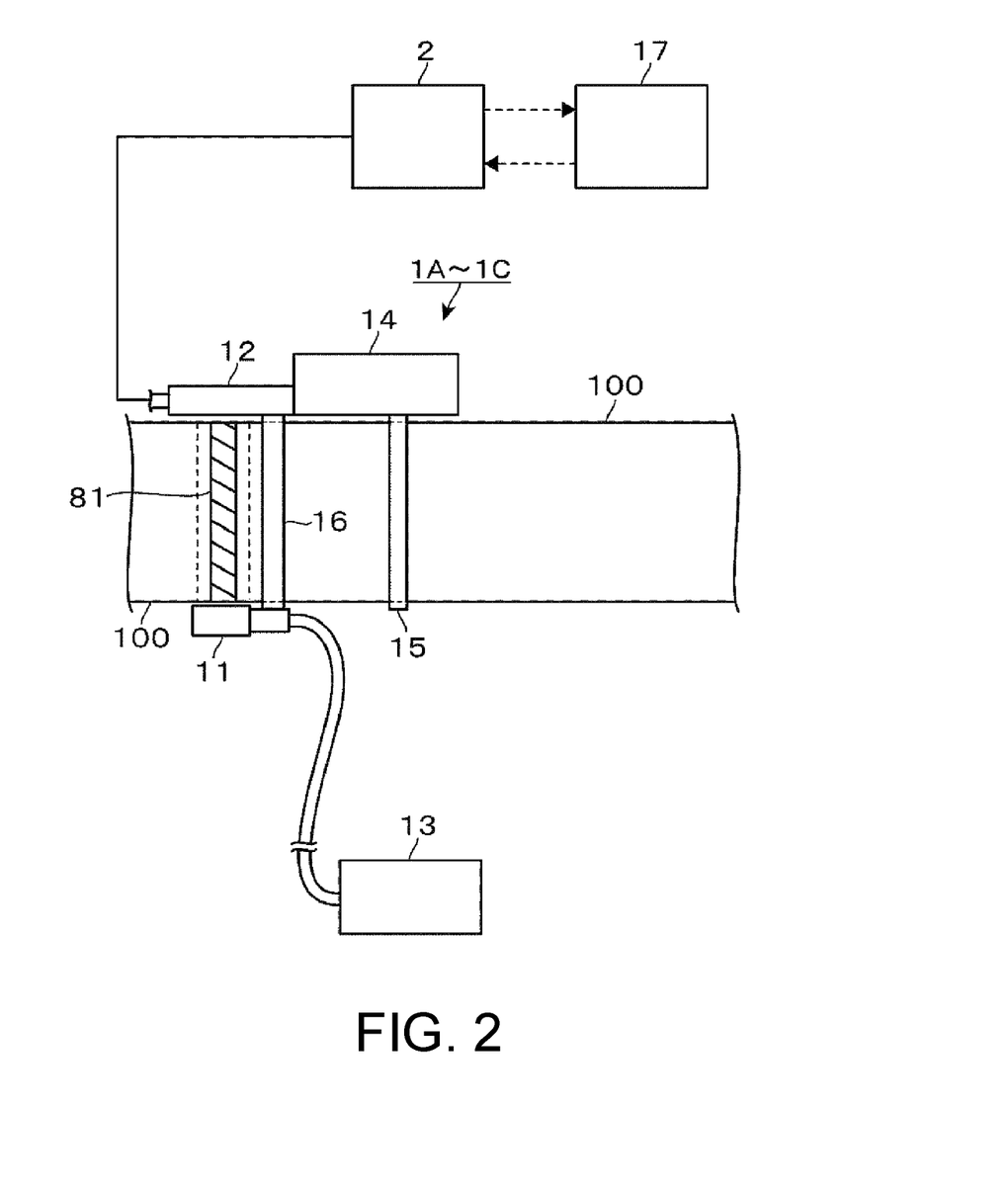
FIG. 2 is a side view of an imaging data acquisition unit.

FIG. 2 shows a configuration example of the imaging data acquisition unit 1. In FIG. 2, there is illustrated an example of acquiring imaging data for a site at which ends of two pipes 100 are connected via a welded portion 81. The imaging data acquisition unit 1 includes a radiation irradiation unit 11 for irradiating radiation in a direction of the welded portion 81 of the pipes 100 and a detector 12 for detecting the radiation transmitted through the welded portion 81. In FIG. 2, reference numeral 13 denotes a device or power supply for irradiating radiation from the radiation irradiation unit 11. For the imaging data acquisition unit 1 of this example, there can be used a flat panel detector (FPD) capable of detecting radiation with a panel-shaped detector without using a film, associating the detected radiation with coordinates set in a detection plane of the detector, and outputting digital data indicating a detection amount of radiation as imaging data.

As described above, the two pipes 100 to be inspected are connected via the welded portion 81 by matching the end of one of the pipes 100 to the end of the other of the pipes 100. The welded portion 81 is welded over the entire circumference of the pipes 100. In FIG. 2, there is illustrated a case in which the welded portion 81 connects two pipes 100, but the imaging data acquisition unit 1 of this example can also be used for inspecting a pipe 100 and a flange, a pipe 100 and an elbow, and a flange and an elbow, for example.

As illustrated in FIG. 2, the radiation irradiation unit 11 and the detector 12 are arranged by a jig 16 so as to face each other across the welded portion 81 to be inspected. When radiation is irradiated from the radiation irradiation unit under this arrangement state, the radiation transmitted through the welded portion 81 is detected by the detector 12, and the above-mentioned imaging data, which is digital data, is acquired based on the transmission intensity of the radiation detected by the detector 12.

The imaging data acquisition unit 1 also includes a moving body 14 for moving the radiation irradiation unit 11, the detector 12, and the jig 16 along a guide 15, which is a movement track arranged externally in the circumferential direction of the pipes 100. Through use of the jig 16 to move the radiation irradiation unit 11 and the detector 12 while maintaining the state in which the radiation irradiation unit 11 and the detector 12 are arranged so as to face each other, the radiation irradiation unit 11 and the detector 12 can be moved in the circumferential direction of the welded portion 81 while remaining in synchronization. The moving body 14 and the guide 15 correspond to a movement mechanism of this example.

The jig 16 of this example can freely adjust a distance between the radiation irradiation unit 11 and the detector 12 in accordance with the outer diameter of the pipe 100.

Length of the movement track formed by the guide 15 is also freely adjustable in accordance with the circumference of the pipes 100.

Further, the imaging data acquisition unit 1 includes a control unit 2, which is an image processing unit for controlling the acquisition of the imaging data and combining the imaging data in a manner described later to create image data, and an operation unit 17 serving as an operation terminal for operating the imaging data acquisition unit 1 and is built from a tablet PC, for example.

Figure 3:
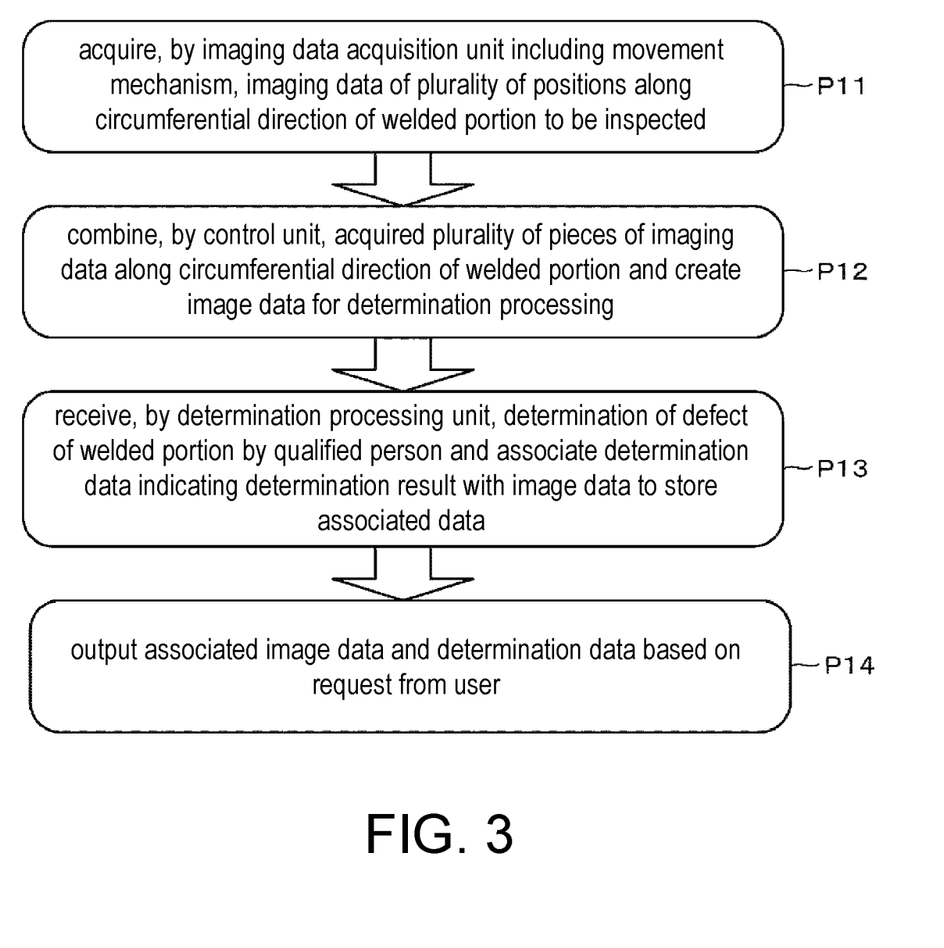
FIG. 3 is a process chart for illustrating an example of an inspection of a pipe welded portion in the inspection system.

Subsequently, there is described, with reference to a process chart illustrated in FIG. 3 and to FIG. 4, an example of inspection processes for performing the radiation transmission test of the welded portion 81 by using an inspection system having the above-mentioned configuration. First, the imaging data acquisition unit 1 acquires pieces of imaging data 90 of a plurality of positions along the circumferential direction of the welded portion 81 to be inspected (Process P11). In the case of distinguishing the pieces of imaging data 90, the pieces of imaging data 90 are distinguished by attaching additional identification symbols A and B.

Figure 4:
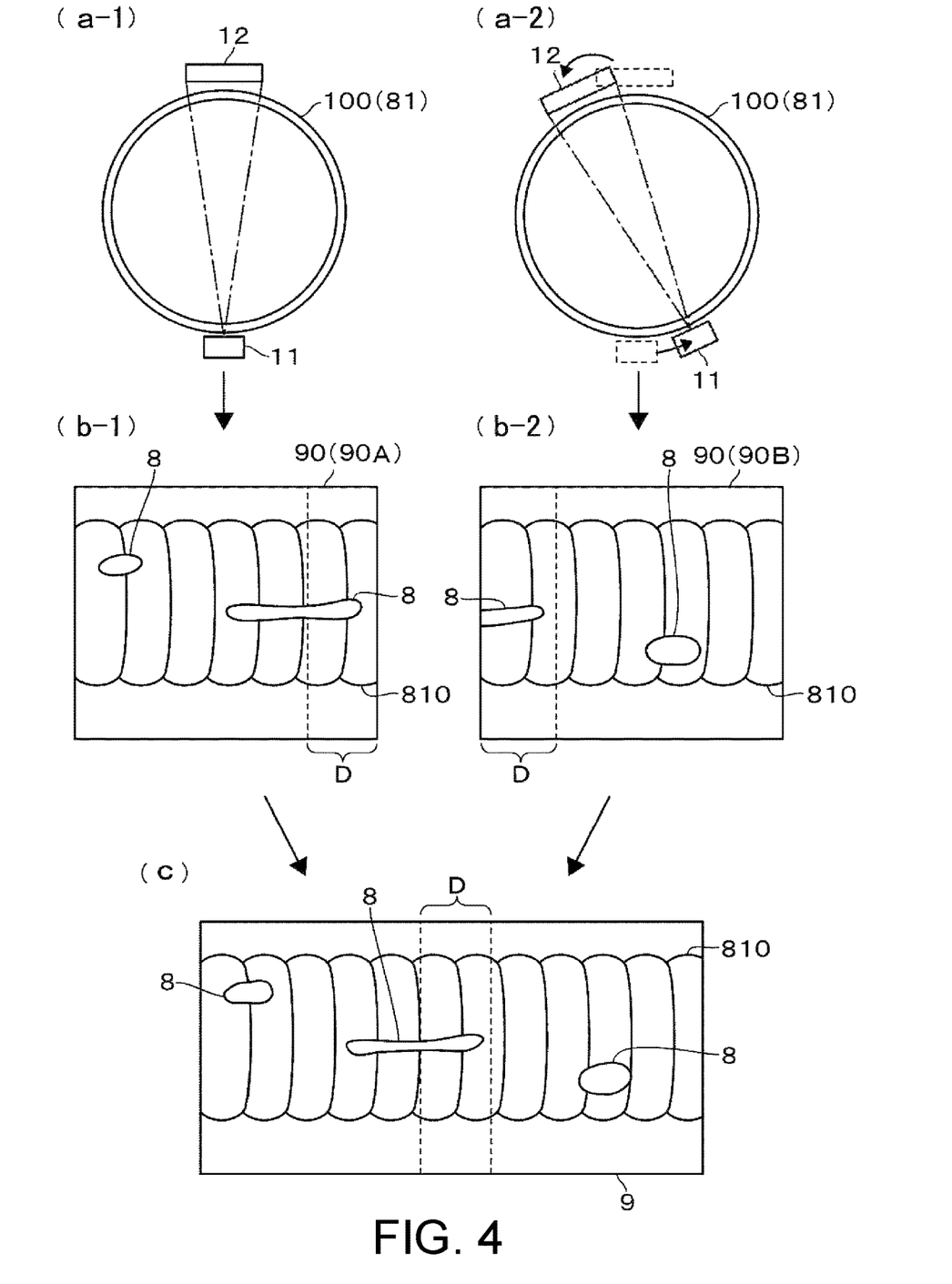
FIG. 4 are explanatory diagrams for illustrating acquisition of imaging data and a method of creating image data.

As illustrated in FIG. 4(*a*-1), for example, the worker performing the radiation transmission test uses the jig 16 to arrange the radiation irradiation unit 11 and the detector 12 so as to face each other across the welded portion 81 of the pipe 100 to be inspected. Then, the welded portion 81 is irradiated with radiation from the radiation irradiation unit 11, the radiation is detected by the detector 12, and imaging data 90A is acquired based on the transmission intensity of the radiation transmitted through the welded portion 81.

As illustrated in FIG. 4(*b*-1), the imaging data 90A is unprocessed data (RAW data) corresponding to an image along a formation direction of the welded portion 81. The imaging data 90A shows the distribution of the transmission intensity of the radiation in a field of view obtained by performing imaging one time under a state in which the radiation irradiation unit 11 and the detector 12 are arranged at the position illustrated in FIG. 4(*a*-1). The imaging data 90A illustrated in FIG. 4(*b*-1) includes a welding line 810 indicating the welded portion 81 and flaw images 8 indicating flaws.

For convenience of description, in FIG. 4 to FIG. 6 and FIG. 8 described later, the images displayed based on the image data 9, determined image data 91 described later, and preliminarily determined image data 92 described later are denoted by reference numerals indicating those pieces of data 9, 91, and 92.

After the imaging data is acquired at the position illustrated in FIG. 4(*a*-1), the imaging data acquisition unit 1 moves the radiation irradiation unit 11 and the detector 12 in synchronization in the same direction along the circumferential direction of the pipe 100 by the moving mechanism. Next, imaging data 90B is acquired at a different position in the circumferential direction of the pipe 100 illustrated in FIG. 4(*a*-2). The imaging data 90B illustrated in FIG. 4(*b*-2) shows the distribution of the transmission intensity of the radiation in the field of view imaged at the position illustrated in FIG. 4(*a*-2).

At this time, the arrangement position illustrated in FIG. 4(*a*-2) is set such that an overlapping region D in which a part of the imaged field of view overlaps between the imaging data 90A acquired at the position illustrated in FIG. 4(*a*-1) and the imaging data 90B acquired at the position illustrated in FIG. 4(*a*-2).

In this way, the imaging data acquisition unit 1 of this example sequentially acquires pieces of imaging data 90 at a plurality of different positions in the circumferential direction of the pipe 100. In FIGS. 4, imaging performed at two positions is illustrated, but a plurality of pieces of imaging data 90 are acquired over the entire circumference of the welded portion 81 of the pipe 100 while the radiation irradiation unit 11 and the detector 12 are further moved.

When the imaging data 90 has been acquired in this manner at a plurality of different positions in the circumferential direction of the pipe 100, the control unit 2 combines those plurality of pieces of imaging data 90 to create the image data 9 illustrated in FIG. 4(*c*) (Process P12). At this time, for example, the above-mentioned overlapping area D can be automatically superimposed by performing the image determination of each piece of imaging data 90 and combining pieces of imaging data 90 such that the parts at which the image matches overlap, and thus image data 9 formed by combining the pieces of imaging data 90 along the circumferential direction of the pipe 100 can be obtained.

From the viewpoint of combining the above-mentioned plurality of pieces of imaging data 90, the control unit 2 included in the imaging data acquisition unit 1 serves as an image processing unit of the inspection system of this example. Further, together with the processing of obtaining the image data 9 from the plurality of pieces of imaging data 90, processing of appropriately deleting the overlapping parts may also be performed.

As a result of the processing described above, image data 9 showing the distribution of the transmission intensity of the radiation in the circumferential direction of the welded portion 81 of the pipe 100 in a region surrounded by the dashed lines in FIG. 2 is obtained. Further, the control unit 2 may add to the image data 9 identification information on the image data 9, for example, information on a welder who has performed the welding, the place in which the welding is performed, and the imaging date and time.

The created image data 9 is transmitted by the determination processing unit 3 via, for example, a portable storage medium such as a USB or a SD card, or via a data communication path. For example, the determination processing unit 3 includes an operation display unit 31 for displaying an image which is based on the acquired image data 9 on a monitor and receiving input of information on a determination result of the image data 9. A qualified person 200 performing a pass/failure determination of the welding result determines the presence or absence of defects in the welded portion 81 of the pipe 100 subjected to the radiation transmission test via the operation display unit 31 of the determination processing unit 3. The determination processing unit 3 stores determination data indicating the result of the determination in association with the image data 9.

Figure 5:
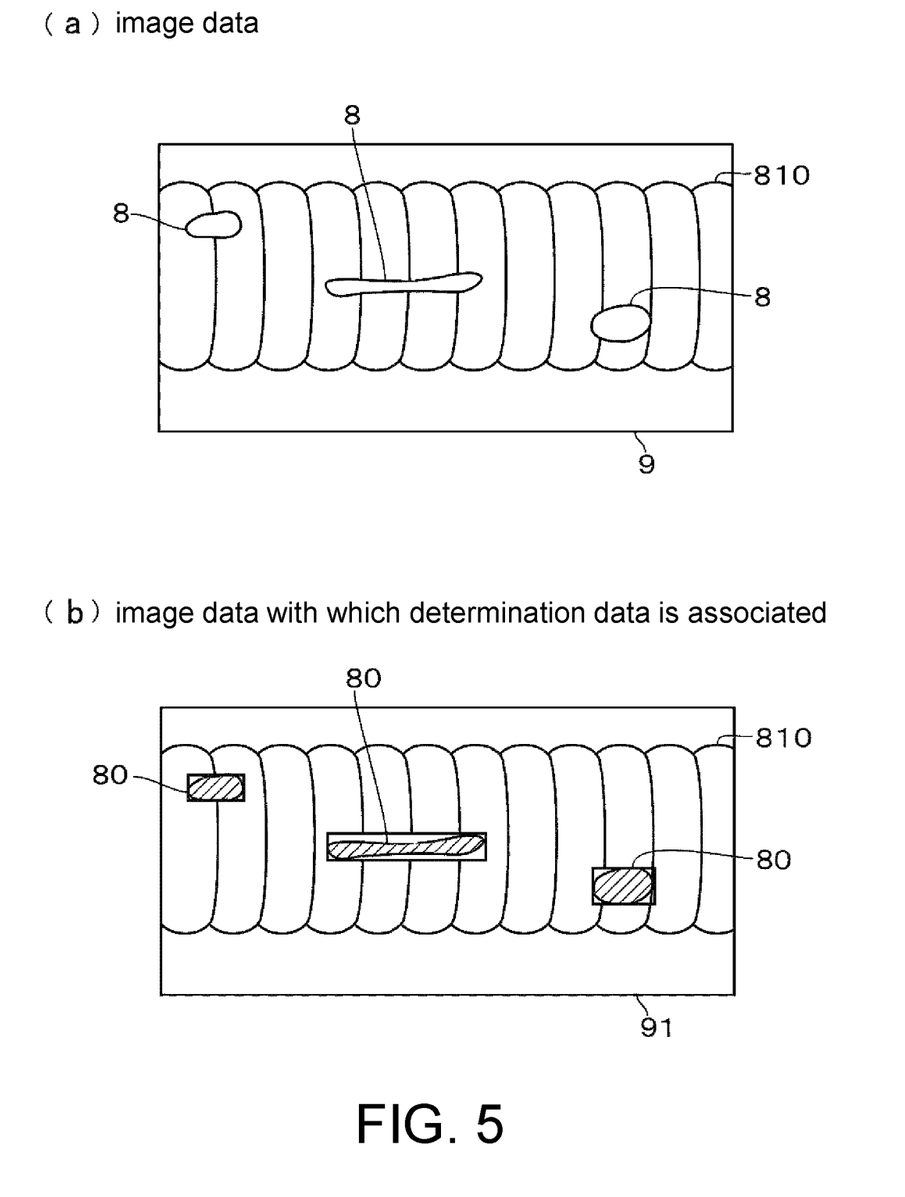
FIG. 5 are explanatory diagrams for illustrating an association between the image data and determination data.

FIG. 5(*a*) and FIG. 5(*b*) shows an example of processing of associating determination data with the image data 9. In FIG. 5(*a*), there is illustrated the image data 9 immediately after being combined by the image processing unit 2.

When a flaw is included in the welded portion 81 imaged by using the imaging data acquisition unit 1, the flaw image 8 appears in the welding line 810 indicating the welded portion 81. For example, the flaw image 8 can be confirmed as a site having a different transmission intensity of the radiation transmitted through the welded portion 81 (site in which the contrast of the image is different).

The qualified person 200 operates the operation display unit 31 while looking at the displayed image, and performs processing (marking up) of attaching a mark 80 so as to enclose the site determined to be defect of the flaw images 8 as illustrated in FIG. 5(*b*). In this way, the qualified person 200 writes the mark 80 indicating the position and size of the flaw image 8 corresponding to a defect in the image data 9.

In the above-mentioned example, all the flaws which have been marked up are determined to be a "defect."

Further, all of the flaws (flaw images 8) that can be distinguished from the image may be marked up, and identification information may be further added to those flaws determined to be defects. At this time, the flaw images 8 to which identification information indicating that the flaw is a defect is added may be displayed as an image having a different color from those of the other flaws that are not defects or having hatching.

In each of the above-mentioned examples, information indicating the position and size of the flaw images 8 identified by the marking up of the flaw images 8 determined to be defects corresponds to the determination data indicating a result of determining a defect.

The image data 9 and the determination data for a defect are associated with each other and stored in a storage unit (not shown) of the determination processing unit 3 (Process P13). The image data 9 with which the determination data has been associated is hereinafter also referred to as "determined image data 91."

When the determination processing unit 3 receives from the user, for example, a person responsible for building the plant, a request to display the determination result of the welded portion 81 for which the determination result is to be checked, the determination processing unit 3 retrieves the determined image data 91 from the storage unit (not shown), and outputs the determined image data 91 as an image (Process P14). The position information on each welding line 810 of each welded portion 81 can be identified based on identification information such as an item number of the pipe 100 or pipe member added to the determined image data 91, a location of the welded portion, the imaging date and time, and a distance from a radiation transmission test start point (usually, with the starting point set as 0, position information is identified by setting 1, 2, and 3 in increments of 10 mm). Further, the output unit which is used by the user to output the determination result may be arranged in a location different from the determination processing unit 3, and configured to acquire the determined image data 91 via the cloud or the like.

According to the inspection system of this embodiment, there are the following effects. In the radiation transmission test of the welded portion 81 of the pipe 100 or the pipe member, radiation is transmitted through the welded portion 81 of the pipe 100 or pipe member to be inspected, and the imaging data 90 of the welded portion 81 is acquired. Hitherto, it has taken time to prepare the radiation transmission test, for example, to place a film on the pipe and enter and exit from a radiation control area each time imaging is performed, but the inspection system of this embodiment can dramatically improve work efficiency. Further, the defect of the welded portion 81 to be inspected is determined by using the imaging data 90, and processing of associating the determination data indicating the determination result with the image data 9 showing the distribution of the transmission intensity of the radiation is performed. Therefore, the determination result can be obtained without using a film, and the work efficiency of the radiation transmission test can be improved by reducing the burden on the worker. Moreover, through use of image data, the image can be enlarged, the contrast can be adjusted, and negative-positive inversion can be performed, for example. Therefore, the inspection accuracy and inspection efficiency can be improved compared to visual determination using a film.

As described above, hitherto, several radiation transmission photographs of the welded portion 81 to be inspected are photographed at the plant construction site along the circumferential direction of the pipe 100, and the qualified person 200 then determines the presence or absence of a defect of the welded portion 81 based on a large number of developed films. Therefore, in the radiation transmission test, not only a storage room for storing a large number of films is required, but a lot of time and effort is taken to, for example, develop the films and handle the chemicals used for developing the films.

In this regard, through acquisition of the imaging data 90A and 90B, which are digital data, it is no longer required to secure a warehouse for storing the films or to handle the chemicals required for developing the films.

In addition, there is also a problem in that when the imaging of the welded portion 81 is performed over the entire circumference of the pipe 100 by manually moving the radiation irradiation unit and the holder supporting the film, from the viewpoint of ensuring a safe distance, it is difficult to provide a large number of imaging apparatus in a limited construction area.

In this regard, as described above with reference to FIG. 2, when an imaging data acquisition unit 1 capable of moving the radiation irradiation unit 11 and the detector 12 is used, remote operation can be performed by the control unit 2 after a safe distance has been secured, and through use of a detector having a higher sensitivity than film, even when a smaller line source is used, more radiation transmission tests can be performed in parallel without compromising work efficiency. Further, the imaging data 90 can be continuously obtained over the entire circumference of the welded portion 81 by moving the radiation irradiation unit 11 and the detector 12 without the worker mounting a film on the welded portion 81 and entering or leaving from the radiation area each time. Moreover, regardless of the skill of the worker performing the imaging, imaging data 90 having little variation in imaging accuracy can be acquired to improve the inspection accuracy. In addition, the imaging data 90 is acquired directly as digital data, and therefore it is easy to check the image on site, and the risk of re-imaging which may occur when imaging fails can be reduced.

Further, with the related-art method of determining a defect by visually evaluating a developed film, it is required to dispatch the qualified person 200 to the site to perform the defect determination, and in a remote area, immediate dispatch may be difficult.

In this regard, the image data 9, which is digital data, can be transmitted to the remote location as well, and the restriction of dispatch of the qualified person 200 can be greatly reduced. From this viewpoint, the determination processing unit 3 illustrated in FIG. 1 may be configured as an independent determination processing apparatus which transmits and receives the image data 9 and the determined image data via the cloud, and only a service for adding the determination data to the image data 9 may be provided.

As an example of the criteria for determining the defect of the welded portion 81 of the pipe 100 described above, American Society of Mechanical Engineers (ASME) Standard B31.3 is known. In Table 1, the types of defects of the welded portion 81 based on ASME B31.3 are shown.

TABLE 1

| | Defect Type |
|---|---|
| 1 | Crack |
| 2 | Lack of Fusion |
| 3 | Incomplete Penetration |

TABLE 1-continued

| | Defect Type |
|---|---|
| 4 | Rounded Indication |
| 5 | Elongated Indication |
| 6 | Undercutting |
| 7 | Concave Surface |

In Table 1, "crack" is a defect in which a crack occurs in the welded portion 81, and "lack of fusion" is a defect in which the welding material is not completely melted and voids occur inside the welded portion 81. Further, "incomplete penetration" is a defect in which the welding material does not completely fill the gap between the pipes 100, and a concave surface is formed in the welded portion 81 on the inner side of the pipe 100. Moreover, flaws remaining on the surface of the welded portion 81 are classified into "rounded indication" and "elongated indication." Examples of other defects include "undercutting," in which a gap occurs between the welding material and the pipe 100 on the surface side, and "concave surface," in which the surface of the welded portion 81 is concave.

Figure 6:
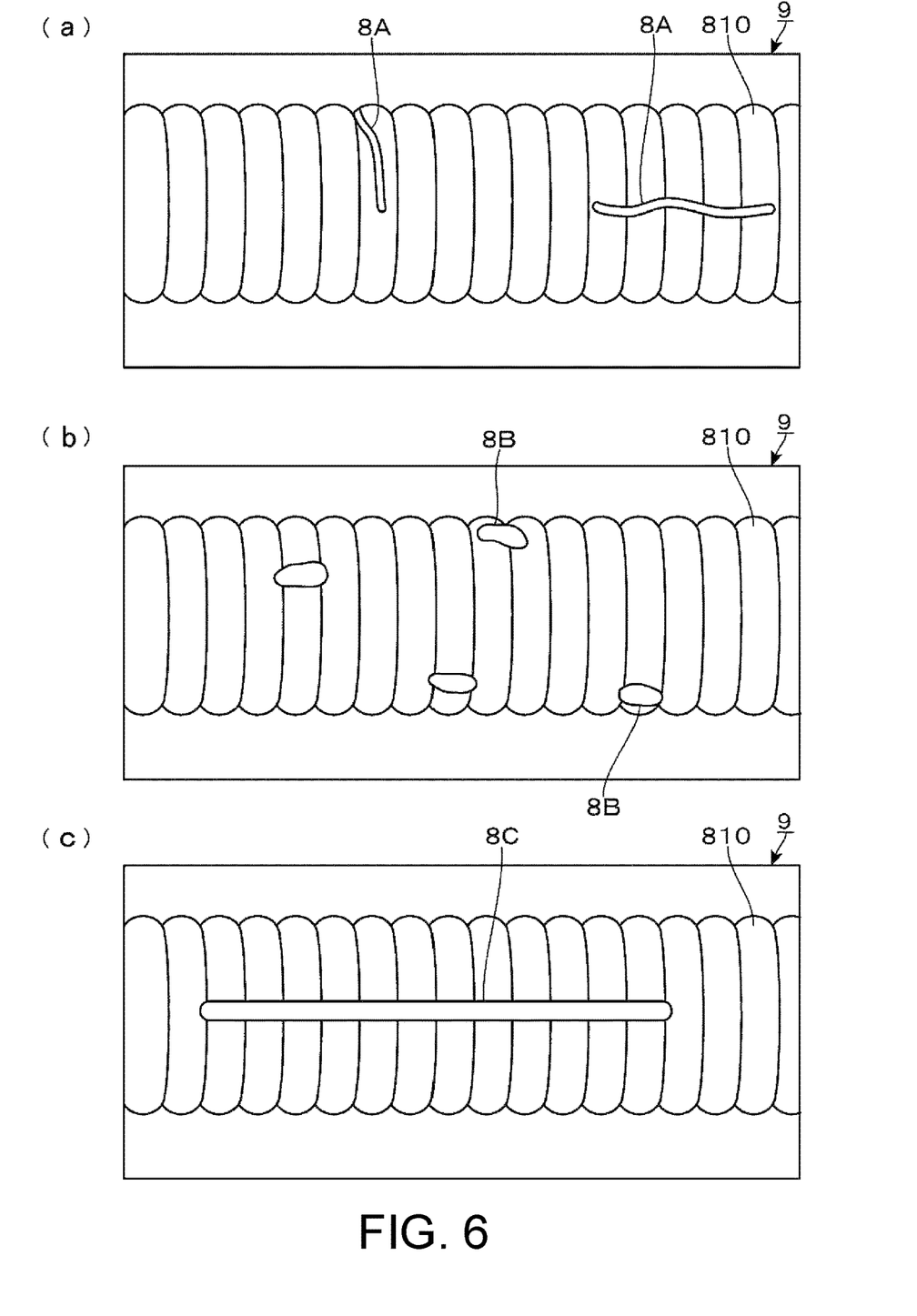
FIG. 6 are explanatory diagrams for illustrating an example of a defect included in the image data.

FIG. 6(*a*) to FIG. 6(*c*) show examples of the image data 9 of the welded portion 81 including those defects. A flaw image 8A included in the welding line 810 of FIG. 6(*a*) shows a flaw corresponding to the defect "crack," and a flaw image 8B of FIG. 6(*b*) shows the "lack of fusion" flaw. A flaw image 8C of FIG. 6(*c*) shows the "incomplete penetration" flaw. In this way, the qualified person 200 distinguishes the position and size of the flaw formed in the welded portion 81 based on the position of the flaw image 8, the size of the flaw image 8, and the shape feature of the flaw image 8 in the image, and when the flaw corresponds to a defect, adds determination data indicating that the flaw corresponds to a defect. Identification information for identifying the type of the defect may be added to the determination data.

When the type of those defects is to be determined, it may be difficult to identify which type of defect the flaw corresponds to simply by looking at the flaw images 8A to 8C included in the image data 9, and a large burden may be placed on the qualified person 200.

Therefore, as illustrated in FIG. 1, the inspection system according to the embodiment of the present disclosure may include the automatic determination unit 5 which distinguishes which type of defect shown in Table 1 the position of the flaw image 8, the size of the flaw image 8, and the shape feature of the flaw image 8 included in the image data 9 corresponds to, and performs markup by adding information for identifying the type of the defect.

Figure 7:
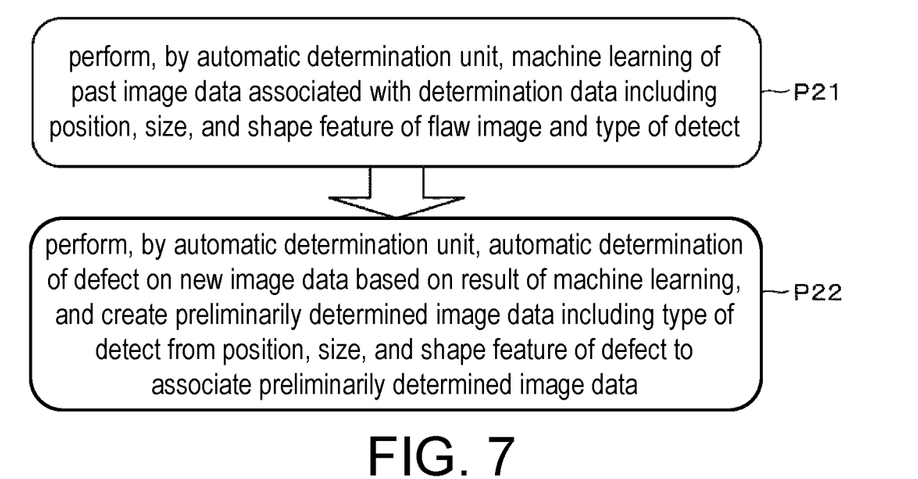
FIG. 7 is a process chart for illustrating an example of automatic determination processing in an automatic determination unit.

An example of automatic determination processing using the automatic determination unit 5 is illustrated in a process chart of FIG. 7. The automatic determination unit 5 acquires the determined image data 91, which is the image data 9 associated with the determination data by the determination processing unit 3, and accumulates a large amount of the determined image data 91 in the storage unit 51.

Then, the automatic determination unit 5 reads out the determined image data 91 accumulated in the storage unit 51, and performs machine learning regarding the position, size, and shape feature of a flaw image 8 determined to be a defect (Process P21). Further, machine learning regarding the position, size, and shape feature of flaw images 8 which are not determined to be a defect may also be performed at this time.

Further, the automatic determination unit 5 determines whether or not a flaw included in new image data 9 corresponds to a defect based on the results of the machine learning of flaws, and constructs an artificial intelligence (AI) determination algorithm, which is a calculation procedure for distinguishing the type of the defect. The AI determination algorithm can, for example, recognize the flaw included in the welded portion 81 based on the area, shape, direction of formation, or trend of a contrast gradation change, for example, of a site which is included in the image data 9 and has a different contrast from those of the surrounding welding lines 810, determine whether or not the flaw corresponds to a defect, and distinguish the type of the defect.

After the AI algorithm is constructed, when new image data 9 is acquired from the imaging data acquisition unit 1, for example, a worker or the qualified person 200 of the radiation transmission test requests the automatic determination unit 5 to automatically determine the image data 9. When the request is received, the automatic determination unit 5 receives image data 9 before the determination processing from the determination processing unit 3, and automatically determines the acquired image data 9 based on the AI determination algorithm.

As a result of the automatic determination, the position of the flaw image 8, the size of the flaw image 8, and the shape feature of the flaw image 8 are extracted, and whether or not the flaw corresponding to the flaw image 8 corresponds to a defect is determined. When it is determined that the flaw corresponds to a defect, the type of the defect is further distinguished.

For the image data 9 determined to include a defect, marking up for associating the image data 9 with a mark 80 including information indicating the type of the defect is performed as preliminary determination data, which is information with which the position of the flaw image 8, the size of the flaw image 8, and the shape feature of the flaw image 8 are identifiable (Process P22). The image data 9 associated with the preliminary determination data is hereinafter also referred to as "preliminarily determined image data 92."

Figure 8:
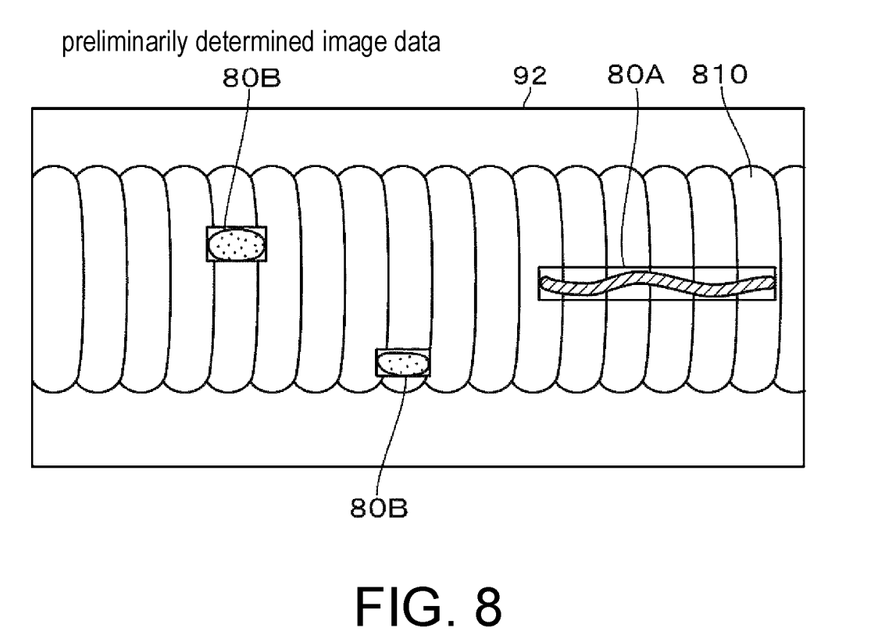
FIG. 8 is an explanatory diagram for illustrating a configuration example of preliminary determination data obtained by the automatic determination unit.

In the example illustrated in FIG. 8, a mark 80A is added to the place corresponding to a defect determined to be a "crack," and a mark 80B is added to the place corresponding to a defect determined to be "lack of fusion." The marks 80A and 80B are associated in advance with the various defects exemplified in Table 1, and marks having different colors or types of hatching are set so as to be visually identifiable from each other.

The image data 9 (preliminarily determined image data 92) to which the preliminary determination data including information indicating the type of the defect has been added is transmitted to the determination processing unit 3 and stored in the storage unit 31.

Figure 9:
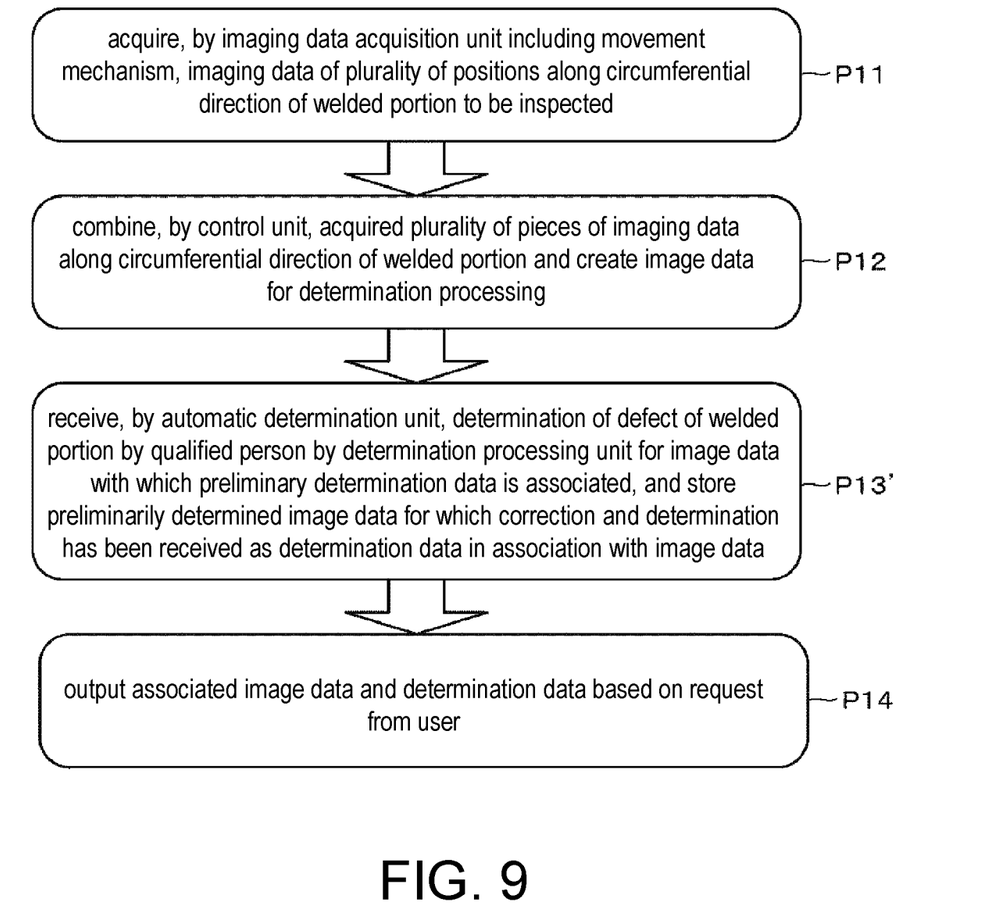
FIG. 9 is a process chart for illustrating an example of an inspection of a welded portion of a pipe including automatic determination processing.

When such preliminarily determined image data 92 automatically determined by the automatic determination unit 5 is used, the determination processing unit 3 displays an image of the preliminarily determined image data 92, as illustrated by Process P13' of FIG. 9, and receives the determination of the defect by the qualified person 200. As a result, based on the determination by the qualified person 200, the preliminary determination data is employed as it is, or the preliminary determination data is corrected, and stored in association with the image data 9 as proper determination data.

Further, the arithmetic unit 52 may be included in the determination process unit 3. That is, the AI determination algorithm may be included in the determination processing unit 3. With such a configuration, the transmission and reception time of the image data 9 can be reduced. In addition, the AI determination algorithm can be used even in locations in which the Internet is not available.

Figure 10:
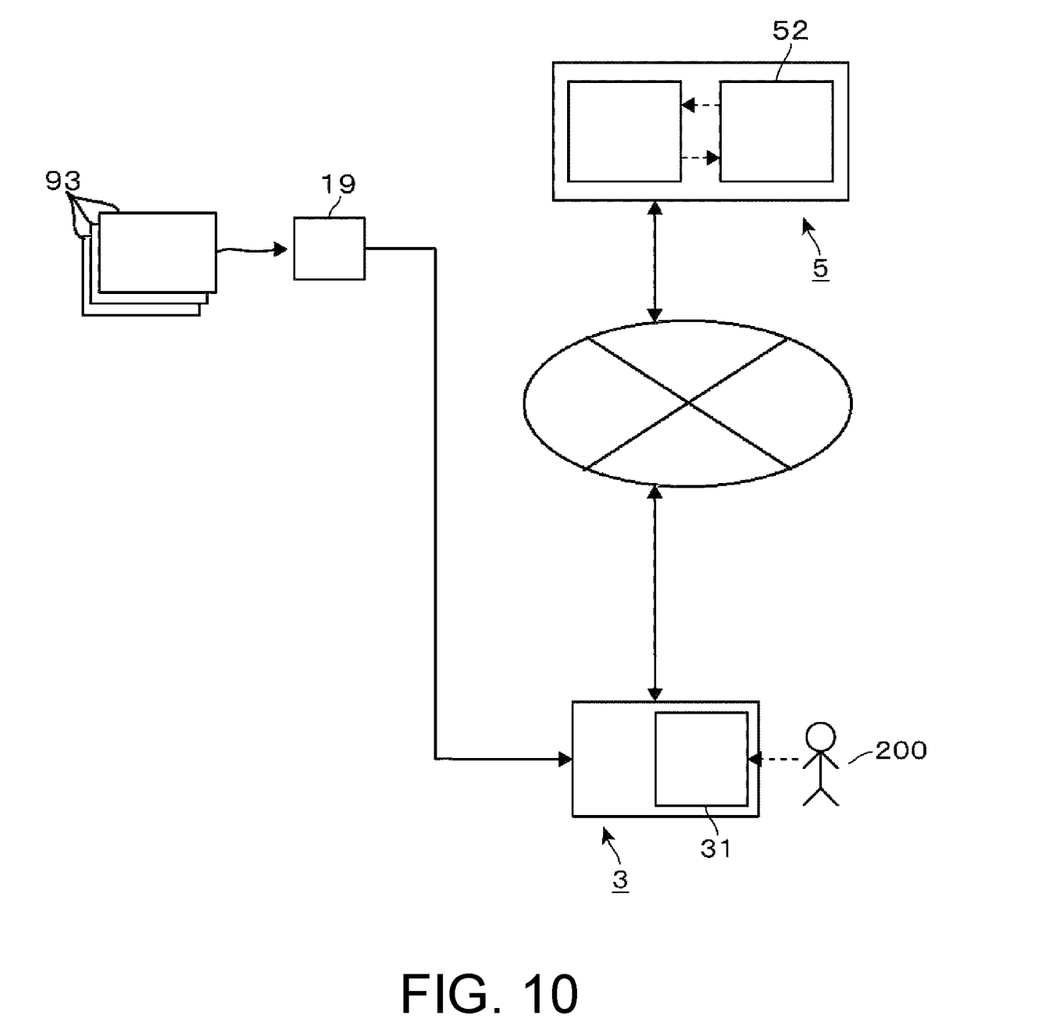
FIG. 10 is a configuration diagram for illustrating another example of the inspection system.

The imaging data acquisition unit 1 described with reference to FIG. 1 and included in the inspection system may be configured by an image reading device for acquiring the imaging data 90 by scanning an imaged analog image. For example, in the example of the inspection system illustrated in FIG. 10, an analog image 93 obtained by irradiating a region including the welded portion 81 to be inspected with radiation and exposing a radiation image transmitted through the welded portion 81 on the film is obtained. The imaging data 90 can be acquired by converting the analog image 93 into digital data by using an image reading device 19 to read the analog image 93. In FIG. 10, there is illustrated an example of acquiring the imaging data 90 from analog images 93 imaged at a plurality of locations by using one image reading device 19. Further, the configuration is not limited to the illustrated example, and those analog images 93 may each be read by a different plurality of image reading devices 19 to acquire the imaging data 90.

Even in the above-mentioned inspection system, image processing of the imaging data 90 read by using the image reading device 19 can be performed, and the obtained image data 9 can be associated with the determination data by the determination processing unit 3. The point that the user can thus easily acquire the determined image data 91 associated with the determination data is the same as that for the inspection system according to the embodiment described with reference to FIG. 1.

The invention claimed is:

1. An inspection system relating to a nondestructive inspection of a defect of a welded portion of a pipe or a pipe member, the inspection system comprising:
an imaging data acquisition unit configured to acquire imaging data obtained by transmitting radiation through the welded portion of the pipe or pipe member to be inspected, wherein the imaging data acquisition unit comprises a radiation irradiation unit configured to irradiate radiation and a detector configured to detect the radiation;
a first processor configured to perform processing of associating, with image data showing a distribution of a transmission intensity of the radiation obtained from the imaging data, determination data which indicates a result of determining a defect of the welded portion to be inspected based on the distribution of the transmission intensity of the radiation, wherein the determination data is associated with information with which a position of a flaw in a welding line included in the image data, a size of the flaw, and a shape feature of the flaw are identifiable, and includes information indicating a type of a defect which is a harmful flaw for which a result of welding of the welded portion is determined to be a failure; and
a second processor configured to create, based on results obtained by performing machine learning of flaws included in past image data with which the determination data is associated, preliminarily determined image data by associating preliminary determination data obtained by automatically determining a type of a predicted defect by identifying the position, size, and shape feature of the flaw in the welding line, with new image data showing a distribution of the transmission intensity of the radiation,
wherein the second processor is configured to transmit the preliminarily determined image data to the first processor, and
wherein the first processor is configured to perform processing of receiving a worker's determination for the preliminary determination data associated with the preliminarily determined image data that the preliminary determination data is correct and associating the resultant preliminary determination data with the new image data as proper determination data.

2. The inspection system according to claim 1,
wherein the radiation irradiation unit is configured to irradiate the radiation in a direction of the welded portion,
wherein the detector is configured to detect the radiation transmitted through the welded portion,
wherein the radiation irradiation unit and the detector are arranged so as to face each other across the welded portion to be inspected, and
wherein the imaging data is acquired as digital data based on the transmission intensity of the radiation detected by the detector.

3. The inspection system according to claim 2,
wherein the imaging data acquisition unit comprises:
a jig for arranging the radiation irradiation unit and the detector so as to face each other across the welded portion to be inspected; and
a movement mechanism configured to move, while maintaining a state in which the radiation irradiation unit and the detector are arranged so as to face each other by the jig, a position to irradiate the radiation in a circumferential direction of the welded portion by moving the radiation irradiation unit and the detector in the circumferential direction with the radiation irradiation unit and the detector remaining in synchronization, and
wherein the imaging data is individually acquired at a plurality of different positions in the circumferential direction of the welded portion.

4. The inspection system according to claim 3, comprising an image processing unit configured to create the image data by combining, along the circumferential direction of the welded portion, a plurality of pieces of the imaging data acquired at a plurality of positions different in the circumferential direction.

5. The inspection system according to claim 1, wherein an analog image obtained by irradiating an area including the welded portion to be inspected with radiation and exposing a radiation image transmitted through the welded portion onto a film is converted to a digital image, and the digital image is used as the imaging data.

6. The inspection system according to claim 1, wherein the first processor is configured to be able to receive processing of correcting the preliminary determination data associated with the image data by the second processor.

7. A determination processing system for performing determination processing relating to a nondestructive inspection of a defect of a welded portion of a pipe or a pipe member, the determination processing system comprising:
a first processor configured to perform processing of associating, with image data showing a distribution of a transmission intensity of radiation obtained by transmitting the radiation through the welded portion of the pipe or pipe member to be inspected, determination data which indicates a result of determining a defect of the welded portion to be inspected based on the distribution of the transmission intensity of the radiation, wherein the determination data is associated with information with which a position of a flaw in a welding line included in the image data, a size of the flaw, and a shape feature of the flaw are identifiable, and includes information indicating a type of a defect which is a harmful flaw for which a result of welding of the welded portion is determined to be a failure; and an second processor configured to create, based on results obtained by performing machine learning of flaws included in past image data with which the determination data is associated, preliminarily determined image data by associating preliminary determination data obtained by automatically determining a type of a predicted defect by identifying the position, size, and shape feature of the flaw in the welding line, with new image data showing a distribution of the transmission intensity of the radiation, wherein the second processor is configured to transmit the preliminarily determined image data to the first processor, and wherein the first processor is configured to perform processing of receiving a worker's determination for the preliminary determination data associated with the preliminarily determined image data that the preliminary determination data is correct and associating the resultant preliminary determination data with the new image data as proper determination data.

8. A determination processing apparatus for performing determination processing relating to a nondestructive inspection of a defect of a welded portion of a pipe or a pipe member, the determination processing apparatus being configured to:

perform processing of associating, with image data showing a distribution of a transmission intensity of radiation obtained by transmitting the radiation through the welded portion of the pipe or pipe member to be inspected, determination data indicating a result of determining a defect of the welded portion to be inspected based on the distribution of the transmission intensity of the radiation, wherein the determination data is associated with information with which a position of a flaw in a welding line included in the image data, a size of the flaw, and a shape feature of the flaw are identifiable, and includes information indicating a type of a defect which is a harmful flaw for which a result of welding of the welded portion is determined to be a failure;

acquire preliminarily determined image data created by, based on results obtained by performing machine learning of flaws included in past image data with which the determination data is associated, associating preliminary determination data obtained by automatically determining a type of a predicted defect by identifying the position, size, and shape feature of the flaw in the welding line, with new image data showing a distribution of the transmission intensity of the radiation; and perform processing of receiving a worker's determination for the preliminary determination data associated with the preliminarily determined image data that the preliminary determination data is correct and associating the resultant preliminary determination data with the new image data as proper determination data.

9. The determination processing apparatus according to claim 8, wherein the determination processing apparatus is configured to be able to receive processing of correcting the preliminary determination data associated with the image data.

10. An inspection method relating to a nondestructive inspection of a defect of a welded portion of a pipe or a pipe member, the inspection method comprising the steps of:

performing processing of associating, with image data showing a distribution of a transmission intensity of radiation obtained by transmitting the radiation through the welded portion of the pipe or pipe member to be inspected, determination data which indicates a result of determining a defect of the welded portion to be inspected based on the distribution of the transmission intensity of the radiation, wherein the determination data is associated with information with which a position of a flaw in a welding line included in the image data, a size of the flaw, and a shape feature of the flaw are identifiable, and includes information indicating a type of a defect which is a harmful flaw for which a result of welding of the welded portion is determined to be a failure; and acquiring preliminarily determined image data created by, based on results obtained by performing machine learning of flaws included in past image data with which the determination data is associated, associating preliminary determination data obtained by automatically determining a type of a predicted defect by identifying the position, size, and shape feature of the flaw in the welding line, with new image data showing a distribution of the transmission intensity of the radiation; and performing processing of receiving a worker's determination for the preliminary determination data associated with the preliminarily determined image data that the preliminary determination data is correct and associating the resultant preliminary determination data with the new image data as proper determination data.

11. The inspection method according to claim 10, wherein the step of performing the processing of associating the determination data with the image data includes receiving processing of correcting the preliminary determination data associated with the image data.

* * * * *